United States Patent [19]

Chen et al.

[11] Patent Number: 4,643,730
[45] Date of Patent: Feb. 17, 1987

[54] RADIATION CURING FORMULATIONS FOR POLYETHYLENE FILM REINFORCEMENT TO PROVIDE REFASTENABLE PRESSURE-SENSITIVE TAPE CLOSURE SYSTEM FOR DISPOSABLE DIAPERS

[75] Inventors: Franklin M. C. Chen; William R. Van Bemmel, both of Appleton, Wis.

[73] Assignee: Kimberly-Clark Corporation, Neenah, Wis.

[21] Appl. No.: 781,089

[22] Filed: Sep. 26, 1985

[51] Int. Cl.⁴ .............................................. B05D 3/06
[52] U.S. Cl. .................................... 604/390; 427/44; 427/54.1
[58] Field of Search ................. 427/44, 54.1; 604/389, 604/390, 387

[56] References Cited

U.S. PATENT DOCUMENTS

| | | | |
|---|---|---|---|
| 3,867,940 | 2/1975 | Mesek et al. | 128/287 |
| 4,020,842 | 5/1977 | Richman et al. | 128/287 |
| 4,043,340 | 8/1977 | Cepuritis | 128/287 |
| 4,049,001 | 9/1977 | Tritsch | 128/287 |
| 4,210,144 | 7/1980 | Sarge et al. | 604/390 |
| 4,291,087 | 9/1981 | Warburton, Jr. | 428/288 |
| 4,296,750 | 10/1981 | Woon et al. | 128/287 |
| 4,387,114 | 6/1983 | Conner et al. | 427/284 |
| 4,514,438 | 4/1985 | Gillberg-LaForce | 427/54.1 |
| 4,539,220 | 9/1985 | Martinelli | 427/44 |

OTHER PUBLICATIONS

W. Oraby and W. K. Walsh, "Elastomeric Electron Beam-Cured Coatings: Structure-Property Relationships, I. Oligomer Structure", Journal of Applied Polymer Science, vol. 23, pp. 3227–3242 (1979).

W. Oraby and W. K. Walsh, "Elastomeric Electron Beam-Cured Coatings: Structure-Property Relationships, II. Chain Transfer Agents", Journal of Applied Polymer Science, vol. 23, pp. 3243–3254 (1979).

James V. Crivello, "Recent Progress in UV Curing", American Chemical Society Division Organic Coating Preparation, vol. 41, p. 560 (1979).

Primary Examiner—John H. Newsome
Attorney, Agent, or Firm—Paul Yee

[57] ABSTRACT

The present invention provides a method for reinforcing a substrate, which includes the step of coating at least a portion of the surface of the substrate with a layer of material that is curable by a high-energy-radiation. The coating material is cured with a suitable source of the high-energy-radiation to form a reinforcement layer affixed to the substrate. The reinforced substrate is particularly useful in the attachment zone of a refastenable, pressure-sensitive tape closure systems.

26 Claims, 8 Drawing Figures

RADIATION CURING FORMULATIONS FOR POLYETHYLENE FILM REINFORCEMENT TO PROVIDE REFASTENABLE PRESSURE-SENSITIVE TAPE CLOSURE SYSTEM FOR DISPOSABLE DIAPERS

FIELD OF THE INVENTION

The present invention relates to a method for reinforcing a substrate. More particularly, the invention relates to a reinforcement for polyolefin film materials to provide a strengthened attachment zone in a refastenable pressure-sensitive tape closure system. The closure system is useful for disposable garments, such as disposable diapers.

BACKGROUND OF THE INVENTION

An economical and effective refastenable adhesive tape closure system has been desired for use in disposable garment articles such as disposable diapers. In diapers, the adhesive tape is employed to fasten the diaper around the waist of an infant. This tape is formulated to be sufficiently tacky to hold the tape securely in place while in storage, and to insure against disengagement or displacement once the diaper is put on the infant. The backing sheet against which the adhesive is fastened are made of a flexible, liquid impermeable film, such as polyethylene. This film is very thin to reduce costs and to provide other characteristics such as flexibility and low rattle. Typically the film is about 0.001 inches (0.00254 cm) thick.

If one desires to inspect or adjust the diaper after the tape has been fastened, the process of peeling the tape from the film backing ordinarily stretches and tears the film because the film has a low tensile load-bearing capability. Further use of the diaper is then impractical; the film is either torn and weakened, or the adhesive areas of the tape are covered by pieces of torn film. Since the film or the tape has been damaged by the removal process, the diaper must be replaced with a new one even though the other diaper components remain substantially undamaged or unsoiled and are otherwise functional.

One suggested solution to the problem has been to use tape with a pressure-sensitive adhesive with moderate tack and peel strength. Such tape would permit peeling the tape off without damage to the film or tape and would thereby provide refastenability. This technique, however, has not been completely satisfactory because the tapes tend to prematurely release during use.

Another suggested technique has been to treat the tape-receiving surface of the film backing sheet with a release coating or, alternatively, interposing in the tape-receiving area another tape component having a release treated surface. Such a technique is disclosed, for example, in U.S. Pat. No. 4,020,842 to Richman, et al.; U.S. Pat. No. 4,043,340 to Cepuratis; and U.S. Pat. No. 4,049,001 to Tritsch. This technique, however, can allow inadvertent and premature release.

A further technique has been to reinforce the adhesive tape attachment zone with a reinforcing layer. For example, U.S. Pat. No. 3,867,940 to Mesek, et al. suggests adhesively laminating a flexible structural material to the film. U.S. Pat. No. 4,296,750 issued Oct. 27, 1981 to Woon, et al. discloses the use of a hot melt adhesive layer to reinforce a plastic film.

Instead of reinforcing the film backing, the strength of the film itself may be increased by increasing the film thickness. This technique, however, is expensive and uneconomical.

The following documents discuss the curing of urethane acrylate oligomers with electron beam radiation: W. Oraby and W. K. Walsh, "Elastomeric Electron Beam-Cured Coatings: Structure-Property Relationships. I. Oligomer Structure", Journal of Applied Polymer Science, Vol. 23, pages 3227–3242 (1979). W. Oraby and W. K. Walsh, "Elastomeric Electron Beam-Cured Coatings: Structure-Property Relationships. II. Chain Transfer Agents", Journal of Applied Polymer Science, Vol. 23, pages 3243–3254 (1979).

James V. Crivello, "Recent Progress in UV Curing", American Chemical Society Division Organic Coating Preparation, Vol. 41, page 560 (1979) discusses the UV-curing of surface coating. Curable resins discussed in this paper include acylates, vinyl esters and N-vinyl pyrrolidone.

U.S. Pat. No. 4,291,087 issued Sept. 22, 1981 to C. E. Warburton, Jr. discloses nonwoven fabrics which are impregnated with a water insoluble binder composed of a polymer curable by electron beam or ultraviolent radiation.

Conventional techniques, such as those taught by the above references, have not provided a sufficiently economical and effective adhesive tape closure system which is readily releasable while providing a closure bond strong enough to avoid undesired, premature release. In addition, these conventional techniques have not been able to effectively reinforce a thin, flexible film substrate without causing unsightly distortions of the substrate material or excessive stiffening of the material.

SUMMARY OF THE INVENTION

The present invention provides an improved method for reinforcing a substrate, which includes the step of coating at least a portion of the surface of the substrate with a layer of material that is curable by a high-energy-radiation. The coating material is cured with a source of the high-energy-radiation to form a reinforcement layer affixed to the substrate. This method is particularly useful for forming a reinforced attachment zone against which a pressure-sensitive adhesive tape can be releasably adhered in a tape closure system of a garment.

The present invention provides an economical and efficient technique for reinforcing a substrate, such as a substrate used for an attachment and securement zone in a tape closure system. The coating material can be readily applied to the substrate and efficiently cured by exposing it to a high energy radiation, such as electron beam radiation or ultraviolet radiation. When employed in the production of disposable diapers, for example, the technique does not cause undesired distortions of the diaper backsheet material and does not excessively stiffen the diaper. As a result, the diaper article can retain its pleasing appearance and feel.

BRIEF DESCRIPTION OF THE DRAWINGS

The invention will be more fully understood and further advantages will become apparent when reference is made to the following detailed description of the invention and the drawings in which.

DETAILED DESCRIPTION OF THE INVENTION

The present invention provides an improved adhesive tape closure system useful for various applications. Such applications include closures or fasteners for diapers, incontinence garments, hat bands, closeable sleeve bands or cuffs, and the like. While the present invention will be more specifically described in the context of a disposable diaper, it will be apparent that the teachings are readily adapted for use in other similar applications, such as those discussed above, all of which are contemplated as being within the scope of the invention.

Figure 1:
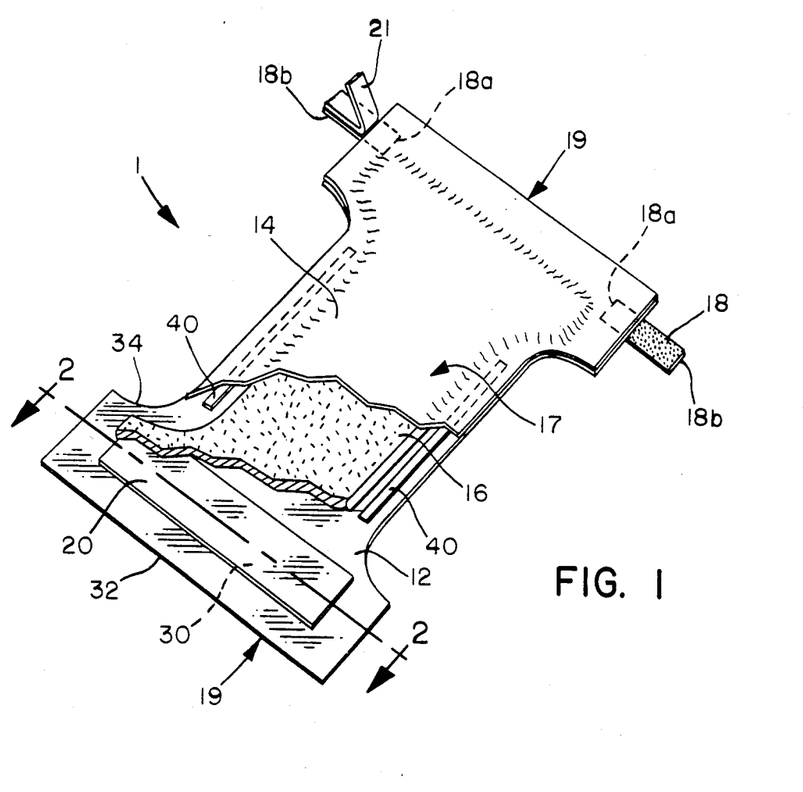
FIG. 1 representatively shows a perspective, sectional view of a diaper having a reinforced backsheet substrate.
Figure 2:
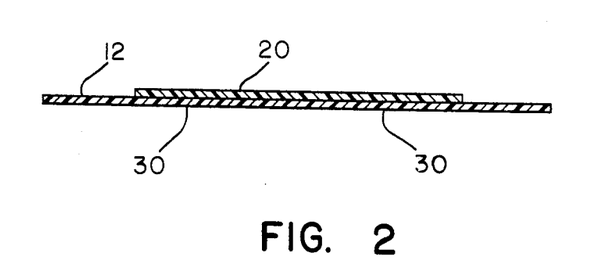
FIG. 2 representatively shows a sectional view taken along line 2—2 of FIG. 1.

Referring to FIGS. 1 and 2, disposable garment, such as diaper 1, is generally comprised of a liquid permeable inner liner 14, a liquid impermeable outer layer or backsheet 12, and an absorbent batt 16 secured therebetween. The inner liner may be any soft, flexible porous sheet which passes fluid therethrough, and may be comprised of a nonwoven web or sheet of polyolefin fibers such as polypropylene, wet strength tissue paper, a spun woven filament sheet, or the like. The liquid impermeable backsheet may be comprised of a thin web or sheet of polyolefin or plastic film material, such as polyethylene, polypropylene, polyvinylchloride or the like. The absorbent batt may be comprised or any suitable absorbent material. Typically, the batt is comprised of a cellulosic material, such as an air-formed batt of wood pulp fiber commonly known as "fluff". Inner liner 14, backsheet 12 and batt 16 may be combined with one another in any suitable manner to form the finished diaper. For example, the elements may be bonded to one another by means of strips or patterns of hot melt or pressure sensitive adhesive, by patterned heat sealing, by strips of double faced pressure sensitive adhesive tape, or the like.

Figure 3:
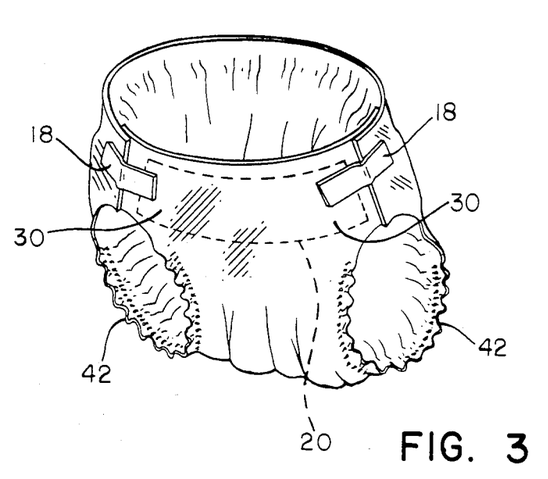
FIG. 3 representatively shows the diaper of FIG. 1 in the approximate configuration assumed when the wearer is placed on the wearer.

The diaper is generally "hour-glass" or I-shaped with a central, narrowed crotch section 17 and waistband sections 19 located at each longitudinal end thereof. Elongate elastic means 40 are typically secured in place adjacent the absorbent batt and on each side thereof to develop gathered elastic leg portions 42 which are conformable with an infant's legs (FIG. 3). The diaper waist bands encircle the infant's waist and are secured together with a pressure-sensitive tape closure system.

The tape closure system includes a pressure-sensitive adhesive tape 18 attached at selected portions of the garment, such as at each of the two corners located at one end of the diaper. The factory attached portion 18a of each adhesive strip is affixed to diaper backsheet 12, and an unattached portion 18b of the adhesive strip is typically covered by some sort of a removable protective strip 21. The unattached portions of the adhesive strip are constructed and configured to adhesively engage predetermined attachment zones located on other portions of the diaper garment. These attachment zones for the adhesive tapes are typically located at the opposite end of the diaper. Attachment zones 30 are generally spaced inward from end 32 and sides 34 of the diaper, and are configured with sufficient areal size to allow a fitting of the diaper around infants having different waist sizes (FIG. 3).

A releasable and refastenable tape closure system has been desired to allow the diaper to be removed and refitted to an infant. For example, one may desire to check the infant for wetness or to remove the diaper to bathe the infant. If a diaper has not been soiled, it can potentially be reused.

The adhesive tapes employed to fasten the diaper around the infant's waist, however, have to be fairly aggressive to provide an adhesive bond adequate to secure the waist portions of the diaper together. Generally, the adhesive bond peel strength is greater than the tensile strength and tear resistance of the diaper backsheet. As a result, attempts to release or peel the tape away from the diaper attachment zones tears away the backsheet material and destroys the ability to refasten the adhesive tapes.

Various techniques have been employed to provide a releasable and refastenable tape closure system. For example, attempts have been made to reduce the "aggressiveness" or bonding strength of the tape adhesive. This technique, however, tolerates only a very narrow "window" of adhesive bond strength because the tear strength of the backsheet material is typically quite close to the minimum adhesive strength needed to maintain a secure closure of the diaper. The backsheet tensile strength is also closely matched to the minimum strength required to resist stresses induced by the movements of an active infant. As a result, the difference in bond strength between an adhesive that tears the backsheet and one that too easily releases is small, and it has been difficult to find an adhesive with a bond strength that consistently remains in the desired range or "window".

An alternative technique has been to use a thicker, stronger and more tear resistant material, such as polyethylene film which measures at least about 0.00381 cm thick. This technique has not been desirable because it significantly raises the manufacturing costs of the garment, decreases the softness and flexibility of the material, and increases the noise generated by the garment during use.

Still another technique has been to reinforce the backsheet material. For example, a layer of hot melt adhesive has been employed to provide a reinforcement, as shown in U.S. Pat. No. 4,296,750 to Woon, et al. While the technique taught by Woon, et al. is effective, it may excessively stiffen the backsheet. As a result, it has been desirable to develop an even more effective and efficient method of reinforcement, which can be employed in a high speed manufacturing operation that can typically produce several hundred diapers per minute.

Figure 4:
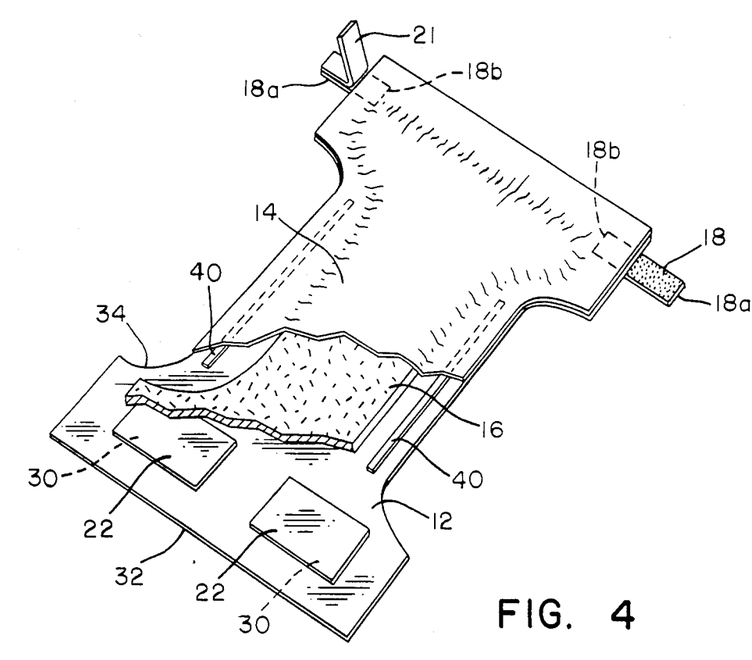
FIG. 4 representatively shows a perspective view of another embodiment of the invention wherein a discontinuous reinforcement is applied to the diaper substrate.

It has been discovered that an attachment substrate, such as the backsheet of a diaper, can advantageously be reinforced by coating at least a portion of the surface of the substrate with a layer of material that is curable by exposure to a high-energy-radiation. Upon exposure to a suitable source of high-energy radiation, the coating material cures to form a reinforcement layer affixed to the substrate. As representatively shown in FIG. 1, the reinforcement layer can form a continuous layer 20, or as representatively shown in FIG. 4, the reinforcement layer can form a discontinuous pattern 22. Generally stated, the attachment substrate is composed of a polyolefin film material which is constructed and arranged to receive adhesive contact with a tape member that has a layer of pressure-sensitive adhesive thereon. The reinforcement layer is affixed to the attachment substrate and is at least in part composed of a polymerized, urethane acrylate oligomer which has been cured by exposure to a suitable, activating high-energy-radiation.

In a particular aspect of the invention, the curable applied coating is composed of a material consisting essentially of an admixture defined by the formula $M_xL_yT_z$, wherein M is at least one compound selected from the group consisting of urethane acrylate acrylic oligomers, acrylated acrylic oligomers and epoxyacrylate acrylic oligomers, L is at least one compound selected from the group consisting of monofunctional acrylate monomers, difunctional acrylate monomers and acrylic monomers, T is at least one compound selected from the group consisting of trifunctional acrylate monomers, "x" ranges from about 30–60 wt. %, "y" ranges from about 30–50 wt. % and "z" ranges from about 0–15 wt. %, with the proviso that the component materials total 100 wt. %.

The coating composition can optionally include chain transfer agents, such as those described in W. Oraby and W. K. Walsh, "Elastomeric Electron Beam-Cured Coatings: Chain Transfer Agents", Journal of Applied Polymer Science, Vol. 23, pages 3243–3254 (1979)., to improve the flexibility of the coating. In addition, the coating composition may include plasticizers, surfactants, and pigments.

In another particular aspect of the invention, the applied coating layer is composed of a material consisting essentially of about 30–70 wt. % of a urethane acrylate oligomer, about 10–40 wt. % of N-vinyl-2-pyrrolidone and about 5–40 wt. % of at least one of the compounds selected from the group consisting of polyethylene glycol diacrylate and propoxylated neopentyl glycol diacrylate.

In a preferred aspect of the invention, the applied coating is composed of a material consisting essentially of about 60 wt. % of a urethane acrylate oligomer, about 20 wt. % of N-vinyl-2-pyrrolidone (NVP) and about 20 wt. % of either polyethylene glycol diacrylate or propoxylated neopentyl glycol diacrylate.

The M-group compounds in the coating material mixture provide high molecular weight reactive molecules which by virtue of their chemical "backbone" structure can contribute adhesion and flexibility to the cured coating layer. The L-group of compounds are reactive diluents, which are usually low molecular weight materials. The diluents are selected for their ability to provide good solvent power and their ability to effectively reduce the viscosity of the oligomer components without excessively retarding the coating cure rate. The molecular weight and the polyol type of the urethane acrylate oligomer are important parameters in the selection of the component. These two parameters can provide better flexibility of the cured film.

Other preferred coating formulations include N-vinyl-2-pyrrolidone and polyethylene glycol diacrylate. The functional groups in N-vinyl-2-pyrrolidone provide good adhesion between the cured coating and the substrate. The ether linkage in polyethylene glycol diacrylate provides flexibility in the film.

The viscosity of the uncured coating material is about 100–10,000 cP, preferably is about 500–5,000 cP, and more preferably is about 1,500–2,500 cP. The optimum viscosity will depend upon the chosen coating application technique.

When employing ultraviolet (UV) radiation to cure the coating material, about 0.1–10 wt. % of a photoinitiator, such as 1-hydroxycyclohexl phenyl ketone, is added to the coating mixture. This photoinitiator is activated and ionized by UV to produce free radicals which operate to polymerize and cure the coating material.

Suitable photoinitiators include those that produce initiating radicals of intramolecular cleavage and those that produce initiating radicals by intermolecular hydrogen-abstraction. Examples of those that produce initiating radicals by intramolecular cleavage are methyl benzoin ether, ethyl benzoin ether, isopropyl benzoin ether, n butyl benzoin ether, 1,1-diethoxyacetophenone, 2,2-dimethoxy-2-phenylacetophenone, 2-hydroxy-2,2-dimethylacetophenone, and 1-benzoylcyclohexan-1-ol. Examples of those that produce initiating radicals by intermolecular hydrogen-abstraction are: 4-chlorobenzophenone, 4-phenylbenzophenone, 4,4-bis (diethylamino) benzophenone, 4-P-Tolytlthiobenzophenone, fluorenone, 2-methylanthroquinone, dibenzosuberone, 2-chlorothioxanthone, 2-methyl-thioxanthone, 2-isopropyl-thioxanthone, 2,4-diethylthioxanthone.

Certain tertiary amine coinitiators can be used to optimize the performance of those intermolecular hydrogen-abstraction type photoinitiators. Examples of the coinitiators are: n-methyldiethanolamine, diethylenetriamine, monethanolamine, diethanolamine, triethanolamine, n-n-dimethylamino ethylmethacrylate, phenthylamine, triethylamine, dimethy ethanol amine, morpholine and ethyl para-dimethylaminobenzoate.

It is also advantageous to include organic peroxide compounds in the formulation. Examples of the organic peroxides are: peroxyformic acid, peroxyacetic acid, 2,4-dichloroperoxybenzoic acid, 12-hydroxyperoxystearic acid, monoperoxysebacic acid, diperoxysebacic acid, diacetyl peroxide, dicaprylyl peroxide, didecanoyl peroxide, diisobutyryl peroxide, diisononyl peroxide, dilauroyl peroxide, dipelargonyl peroxide, dipropanoyl peroxide, dibenzoyl peroxide, di(p-chlorobenzoyl) peroxide, di(2,4-dichlorobenzoyl) peroxide, succinic acid peroxide, benzoyl isobutyryl peroxide, benzoyl acetyl peroxide, t-butyl peroxyacetate, 5-butyl peroxygenzoate, 5-butyl peroxy (2-ethylhexanoate), 5-butyl peroxyisobutyrate, o,o-tert-butyl o-isopropyl monoperoxycarbonate, t-butyl peroxypivalate, 2,5-dimethyl-2-5-di(-benzoylperoxy) hexane, t-butyl peroxy (2-ethylbutyrate), 2,5-bimethyl-2,5-di(2-ethylhexanoylperoxy) hexane, di-t butyl diperoxyphthalate, o,o-tert butyl o-hydrogen monperoxy maleate, di-sec-butyl peroxydicarbonate, diisopropylperoxy-dicarbonate, dicyclohexyl peroxydicarbonate, t-butyl peroxycrotonate. N,N-diethyl t-butyl peroxycarbamate, and N,N-diphenyl t-butyl peroxycarbonate, acetyl cyclohexybulfomyl peroxide, and t-butylazoformamide.

For the purposes of the present invention, the term high-energy-radiation is intended to mean a stream of subatomic particles or photons having wavelengths equal to or less than the wavelength of electomagnetic radiation commonly referred to as UV radiation. The determination of wavelength is done in accordance with the principles of quantum mechanics or classical electromagnetic theory, whichever is applicable. In addition, such high-energy radiation is capable of "ionizing" chemical compounds. In particular, the radiation is capable of breaking particular chemical bonds within the coating material. In a described embodiment of the invention, this breaking of chemical bonds creates free radicals which operate to cure the coating material. Thus, high-energy-radiation would include electromagnetic radiation having wavelengths of 0.4 micrometers or less, such as UV radiation and X-rays, and would also include subatomic particle beams, such as beams of electrons.

The backsheet substrate in a diaper is generally composed of a flexible, thin material, such as a plastic film. The substrate is sufficiently flexible to allow the diaper to conform to the body shape of the wearer and to accommodate the ordinary movements of the wearer. For example, in a disposable diaper, the substrate is comprised of a liquid impermeable backsheet which is composed of a polyolefin film, such as polyethylene, polypropylene or the like. Typically a plastic film measures about 0.001 in. (about 0.00254 cm) thick, but can be varied to have a thickness within the range of about 0.0005–0.002 in. (about 0.00127–0.00508 cm). In the manufacture of diapers, the backsheet ordinarily has a peel tear strength which is less than the stress generated on the film when a person peels away an attached adhesive tape to break and release the adhesive bond between the tape and backsheet. In other words, the tear strength of the substrate by itself is less than the peel adhesion value of the pressure sensitive adhesive tape. The process of peeling off the adhesive tape tears the substrate material apart. In addition, some of the torn substrate generally separates and remains attached to the adhesive tape.

In the present invention, the combination of the substrate and the cured reinforcement coating layer advantageously provides a total combined tear strength at the tape attachment zone which is greater than the peel adhesive value of the pressure sensitive adhesive. Thus, when the adhesive tape is peeled away, the substrate does not actually tear apart, although there may be some stretching or other deformation of the substrate material.

It is important that the cured coating forms a strong cohesive bond with the substrate which is sufficient to substantially prevent separation or delamination of the substrate away from the reinforcement coating layer when an attached adhesive tape is peeled away or otherwise released and removed. The bond strength between the substrate and the reinforcement layer should have a cross-cut adhesion test value of at least about 15. Preferably, the cross-cut adhesive test value is at least about 18 and more preferably is at least about 20. The cross-cut adhesion test is described in more detail below.

To further adapt the reinforced substrate for use on a disposable garment, the reinforced substrate should be configured with sufficient flexibility and elasticity to be conformable to the wearer and to accommodate the active movements of the wearer. A measure of the flexibility of the reinforcement layer is provided by a crease test which is described in more detail below. The crease test value is at least about 0.002 in (0.00508 cm), preferably is at least about 0.004 in (0.01016 cm) and more preferably is at least about 0.006 in (0.01524 cm) to provide improved performance.

A measure of the elasticity of the reinforced substrate is provided by a tensile elongation test which is described in more detail below. The tensile elongation test value of the reinforced substrate should be at least about 40%, preferably is at least about 60% and more preferably is at least about 80%.

A refastenability test is employed to determine the peel tear strength of the reinforced substrate. The refastenability test provides a measure of the ability of the reinforced substrate to resist excessive deformation and tearing when an adhesive tape is adhesively fastened and then peeled away. This test is described in further detail below. The reinforced substrate should have a refastenability test value of at least about 600 gm, preferably at least about 700 gm and more preferably at least about 800 gm.

A polyethylene film suitable for use in the present invention and for use in the following testing is a 0.001 in thick polyethylene film that has been embossed. The embossment produces a film having an embossed thickness measurement of about 0.0176 in (about 0.447 mm). This film has a tensile strength of about 125 g/in at 1% elongation and has about 704% elongation at break, as measured in the cross-machine direction (TD) employing the ASTM D 882 test method. The film also has a Dart Impact Test value of less than about 40 g, as determined by employing the ASTM D 1709-75 test method. A suitable embossed polyethylene film is available from Clopay Corporation located in Cincinnati, OH. The high-energy-radiation curable coating of the invention is applied to a surface opposite to the female embossed side of the film, and a selected adhesive tape is appointed for attachment to the female embossed side of the film.

Cross-cut Adhesion Test

To enable a cured coating to reinforce a thin film substrate, there should be good adhesion between the substrate and the coating. The cross-cut adhesion test provides a measure of the adhesion strength between the coating and the substrate. This test involves the steps of forming a layer of cured coating on a substrate, cutting a standard cross-hatch pattern through the cured coating layer, adhering a strip of pressure sensitive testing tape over the cross-hatch pattern, and peeling the testing tape from the coating surface. The percentage of coating layer squares remaining on the substrate is recorded.

A standard cross-hatch pattern is comprised of a 5 mm×5 mm square which is cross-hatched to form twenty-five 1-mm squares in the cured coating. A conventional cross-cut tester available from BYK Chemie located at Wallingford, CT may be employed to cut the cross-hatch pattern.

The film substrate is a 0.001 in thick, embossed polyethylene film secured to a solid support surface, for example, with double-sided adhesive tape, so that the cured coating can be cut without stretching the film material. A suitable support surface would be a piece of smooth, 2-ply card stock, and the adhesive tape should be sufficiently strong to hold the polyethylene film securely to the card stock during the test. To determine the thickness of the coating the thickness of the coating/film substrate composite and the thickness of the film substrate alone are measured with calipers. The film thickness is then subtracted from the film/coating composite thickness.

A 2-in square of the coating film is adhered onto a smooth, flat cardboard backing composed of 2-ply rag card stock with the double sided tape such that the coating is facing outward and the uncoated side of the film is adhered to the card stock. Four cross-hatch patterns are cut into the 2-in square of coating using sufficient pressure to penetrate completely through the coating layer. A piece of 3M, Scotch brand 610 or 810 transparent tape is placed over each cross-hatched pattern on the 2-in square test specimen. The tape is adhered by rubbing with a pencil eraser. The Scotch brand tape is peeled from the coating as quickly as possible employing a 180° peel technique in which the tape is essentially doubled back on itself. For this test, the thickness of the cured coating layer should be within the range of 0.001–0.002 in.

Crease Test

The crease test is employed to evaluate the brittleness of a cured coating on a thin, flexible substrate, such as a 0.001 in. thick, embossed diaper polyethylene film. The composite structure of the cured coating layer on the film substrate is folded over back onto itself, with the coating on the outside of the folded structure. The folded edge is creased by placing a 2650 gram weight with a bottom area of 3,344 mm$^2$ on the crease. This weight exerts a pressure of about 1.1–1.2 psi (about 7.6–8.3 kPa). If the coating does not fracture, the coating thickness is noted and a thicker coating thickness is tested. The higher the coating thickness value reported, the less brittle is the coating. For example, a coating that fractures at 0.002 in (0.0058 cm) is more brittle than a coating that breaks at 0.005 in (0.0127 cm) but not at 0.002 in (0.00508 cm). The value reported is the maximum coating thickness which does not fracture when creased in the manner described above.

Tensile Test

Tensile testing is performed in accordance with the ASTM D 638 test method specifications, which employs a 0.05–0.11 in (0.13–0.28 cm) thick sample of the high-energy-radiation cured resin. Samples are prepared by pouring the resins into a mold made from glass plates and curing the resin with radiation directed through the top and bottom of the mold. Standard tensile test specimens are then cut from these cured samples.

Refastenability Test

The tape refastenability test measures the strength of a 0.001 in thick, embossed polyethylene film which has been reinforced with the cured coating layer of the invention. A tape is applied to that surface of the film which is opposite to the surface covered by the coating layer. The tape is then peeled from the film at a constant rate with a machine that measures the peel force of the tape. If the tape is peeled from the film without stretching or tearing the film, the mean peel force is recorded. If the film stretches, tears or delaminates from the reinforcement coating, the failure mode is noted and no peel value is recorded.

Figure 8:
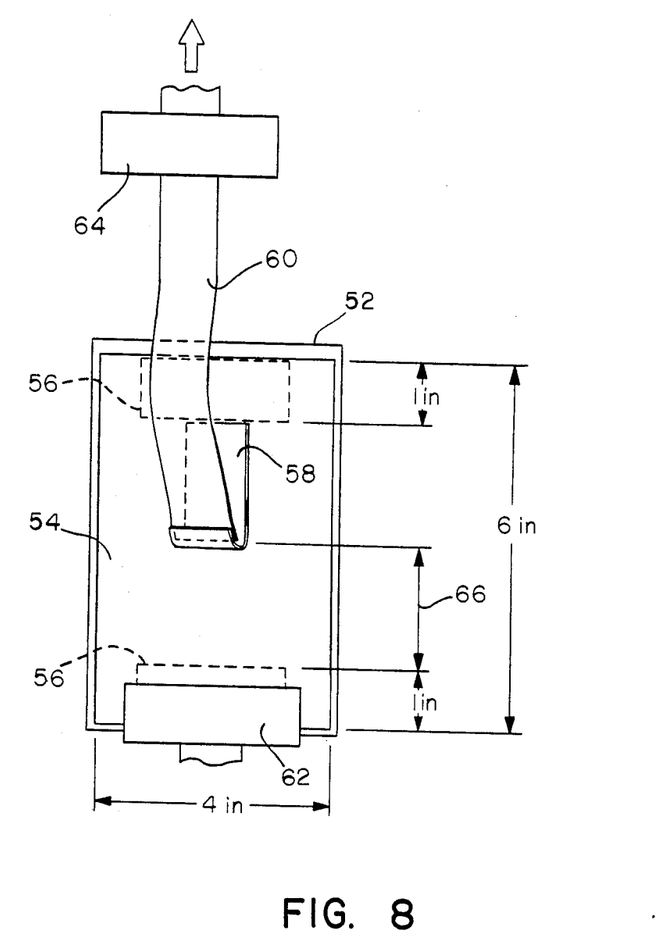
FIG. 8 schematically shows the experimental configuration for a refastenability test.

With reference to FIG. 8, the tape refastenability test procedure employs a test specimen 54 measuring 4×6 in with the 6 in dimension running in the longitudinal direction along which the testing force is applied. The test specimen is anchored to a 6×4×1/16 in stainless steel plate 52 by adhering the 4 in long ends of the test specimen with a suitable, high strength, double sided tape 56. The double sided tape is 1 in wide and 2–2.5 in long, and has sufficient adhesive strength to secure the ends of the test specimen to the steel plate during the course of the test. The double sided tape is located between the test specimen and the steel plate, and the adhesion is produced by rolling over the composite with a 4.5 lb, 1.75 in wide roller. The roller is rolled over the double sided tape region 2 times at a rate of 1 ft/min.

A 1×8 in leader strip 60 composed of a material sufficiently strong to withstand the stresses of this test without breaking, such as brown kraft wrapping paper, is connected to a piece of test tape 58 with an overlap of approximately 0.25 in. The test tape is then adhered to test specimen 54 as illustrated in FIG. 8 to provide a standard gauge length 66 which measures 1 in. The test specimen is then placed in the jaws of a tensile testing machine, such as an Instron machine. As illustrated in FIG. 8, the lower Instron jaws 62 clamp the portions of the steel plate and the test specimen which are adhered together by the double sided tape. The upper Instron jaws 64 attach to the end of the leader strip. The Instron machine settings are a crosshead speed of 300 mm/min; a chart speed of 150 mm/min; a jaw separation of 8 in; and a full-scale load of 2000 gm. The test tape is then pulled back on itself 180° with the Instron machine to peel the test tape away from the film substrate. A Microcon II data processing instrument manufactured by Instron Corporation is operably connected to the Instron machine, and employed to record and display the average peel load in grams. The test is performed in a standard conditioning atmosphere of 50%, plus or minus 2%, relative humidity and 23° C., plus or minus 1° C.

The tape refastenability test may be varied to increase the sensitivity of the test. In the standard test, the testing tape has a average peel strength of about 500 gm/in and the gauge length is 1 in. To increase the severity and sensitivity of the test, the average peel strength of the testing tape can be increased to about 700 gm/in, or the test gauge length may be increased to 2 in, or both.

In the method of the invention, liquid coating material is applied to a substrate, such as the backsheet, by a suitable process, such as a roller application process or a spray application process. Preferably, the backsheet material is coated in a continuous, in-line process, as representatively shown in FIG. 5. In the shown embodiment, a polyethylene backsheet material 70 is unwound from a supply roll 72 and carried along a conveyor, which includes guide rollers 86. A roller-type applicator 74 applies a continuous or discontinuous strip or other pattern of coating material of desired width and thickness to the backsheet. Reservoir tank 80 supplies coating material through suitable fluid conduits to applicator tank 82. Applicator roll 74 contacts the coating material within applicator tank 82 and applies it to the surface of sheet 70. Alternatively, a spray applicator sprays a desired strip or other pattern of coating material in a selected width and thickness onto the backsheet.

Figure 5:
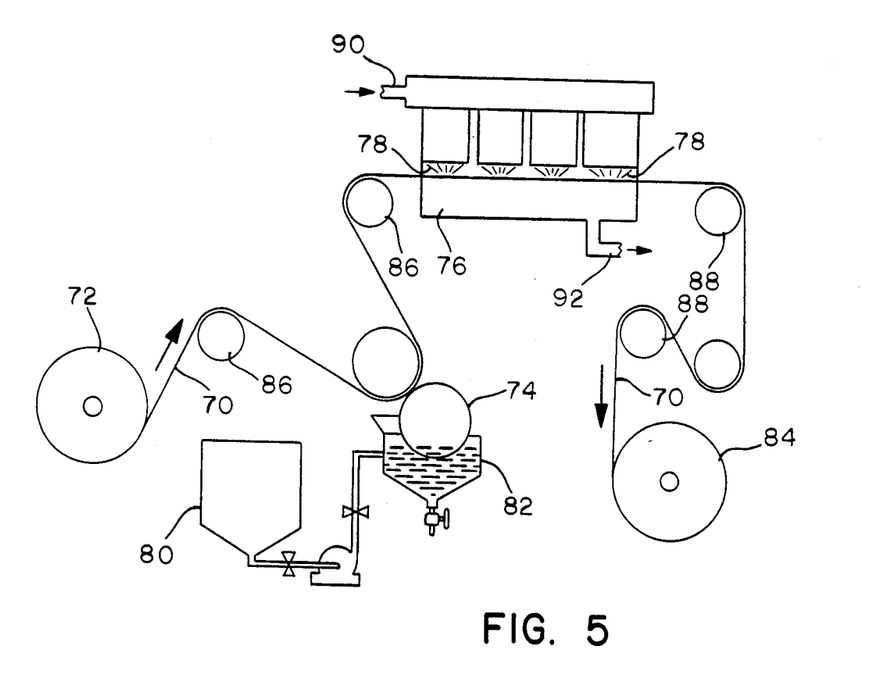
FIG. 5 schematically shows an apparatus for applying a coating layer onto a substrate material.

The conveyor then transports the backsheet material to a curing zone 76 where the coating material is bombarded with a high-energy ionizing radiation 78, such as UV radiation or EB radiation. The residence time of the backsheet material in the curing zone and the intensity of the incident high-energy radiation are adjusted to suitably cure the coating material. Upon curing, the coating material forms a solidified, substantially non-viscous reinforcement layer that is cohesively bonded to the substrate.

The conveyor moves sheet 70 out from curing zone 76. Guide rollers 88 direct the sheet onto takeup roll 84. Cooling air is directed into the curing apparatus through inlet 90, and exhaust air is removed from the apparatus through outlet 92.

The curable resins employed to reinforce the film substrate of a disposable diaper are composed of a mixture of reactive chemicals which is capable of being polymerized by the generation of free radicals in the mixture. These free radicals are generated by a high energy radiation, such as ultraviolent radiation or electron beam radiation.

An important component in the formulation of the curable resins is the urethane acrylate acrylic oligomer, the acrylated acrylic oligomer, the epoxyacrylate acrylic oligomer, or a combination of these resins. The chemical structure of the urethane acrylate oligomer resin is as follows:

The chemical structure of the acrylated acrylic resins is as follows:

The chemical structure of the epoxyacrylate resins is as follows:

The acrylic oligomers are composed of high molecular weight reactive molecules which have a chemical "backbone" structure and provide adhesion and flexibility to the cured coating film. The molecular weight of the acrylic oligomer is an important parameter in the selection of this component of the mixture. For example, a higher molecular weight urethane acrylate oligomer provides greater flexibility in the cured film. To provide improved performance, the acrylic oligomer has a molecular weight of at least about 1000 and preferably has a molecular weight of at least about 4000. This molecular weight is calibrated against polystyrene standards.

A suitable urethane acrylate oligomer is Chempol 19-4827 which is available from Radcure, Inc., Port Washington, Wis. This material is a 100% solid, general purpose acrylated aromatic urethane which may be cured by exposure to either ultraviolet light or electron beam radiation. The molecular weight of this oligomer is about 1500.

The resin formulation includes reactive diluents, which are usually low molecular weight materials selected for their solvent power. The diluents should be able to effectively reduce the viscosity of the oligomer components to facilitate application onto a substrate. The diluents, however, should not excessively retard the cure rate of the coating. Examples or reactive diluents which can be used in the formulations of the invention are listed in Table 1.

TABLE 1

REACTIVE DILUENTS

| Chemistry Name | Trade Name | Supplier |
|---|---|---|
| Tripropylene Glycol Diacrylate | Sartomer SR-306 | Atlantic Richfield Co. (ARCO) |
| Propoxylated Neopentyl Glycol Diacrylate | Photomer 4127 | Diamond Shamrock |
| Polyethylene Glycol Diacrylate (400) | Sartomer SR-344 | ARCO |
| N—Vinyl-2-Pyrrolidone | | Poly Science, Inc. |
| | V-Pyrol | GAF Co. |
| Isooctyl Acrylate | Sartomer SR-440 | ARCO |
| 2-Phenoxyethyl Acrylate | Sartomer SR-339 | ARCO |

The functional groups in N-vinyl-2-pyrrolidone provide good adhesion between the curred coating and the substrate. The ether linkage in polyethylene glycol diacrylate provides flexibility to the cured coating.

Examples of cross-link reactants which can be used in formulating the coating material of the invention are listed in Table 2.

TABLE 2

CROSS-LINK REACTANTS

| Chemistry Name | Trade Name | Supplier |
|---|---|---|
| Trimethylolpropane Triacrylate | Sartomer SR-351 | ARCO |
| | Chempol 19-6006 | Radcure, Inc. |
| Polyethertriacrylate | Chempol 19-6008 | Radcure, Inc. |

A photoinitiator which can be used in the formulation of the coating material of the invention is 1-hydroxycyclohexyl phenyl ketone, such as Irgacure 184 manufactured by Ciba Geigy. Bombardment of this material with ultraviolet radiation produces an aliphatic hydroxycyclohexyl free radical, which is highly reactive. Due to its saturation, however, the free radical has a lower tendency to form colored by-products when compared to the free radicals generated by other commercial photoinitiators. A suitable concentration of the photoinitiator in the coating formulation is about 4 parts per hundred (pph).

A suitable source of ultraviolet radiation is provided by an American ultraviolet model Porta-Cure 1000 available from the American Ultraviolet Co., Chatham, N.J. This equipment provides about 200 watts/in and has a lamp which measures 6-in in length. A suitable separation distance between the lamp and the coated substrate is about 8 in.

When employing electron beam (EB) curing, a suitable source of electron beam radiation is the electron beam equipment model CB200-45-50-750J available from Energy Sciences, Inc., Woburn, Mass. This equipment is about 45 cm wide and has an acceleration voltage which ranges from about 150-200 KV. The maximum product speed is about 1320 ft/min (670 cm/sec).

Figure 6:
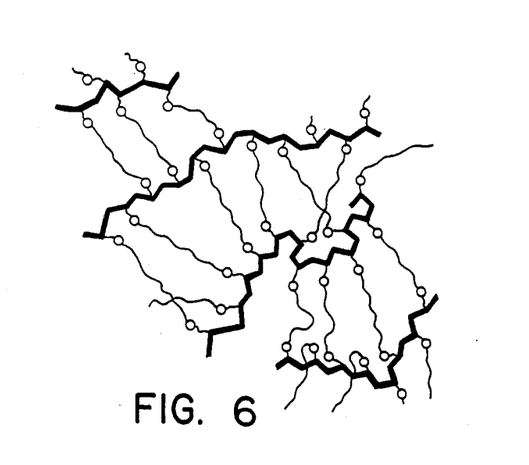
FIG. 6 representatively shows a multi-rayed, star-shaped cross linked structure.

The urethane acrylate oligomers are capped at both ends with highly active acrylate groups. Upon curing and copolymerization with the other acrylic monomers, these highly active acrylate groups become branch points in a network formed within the cured coating. This network is generally represented by a multirayed, star-shaped cross-link structure, which is representatively shown in FIG. 6. The flexibility of the cured coating is dependent upon the molecular weight of the oligomer.

The following examples are presented to provide a further detailed description of the invention. The materials, proportions and techniques described therein are intended to provide illustrative examples of particular aspects of the invention, and are not intended to specifically limit the scope of the invention.

EXAMPLES

In the following tables and examples, the components parts of the resin formulations are indicated as follows:

| Letter Desig. | Chemical Name | Trade Name | Vendor |
|---|---|---|---|
| A | Urethane Acrylate Oligomer | Chempol 19-4827 | Radcure |
| B | Urethane Acrylate Oligomer | Uvithane 783 | Morton Thiokol |
| C | Urethane Acrylate Oligomer | Uvithane 782 | Morton Thiokol |
| D | Polyether Triacrylate | Chempol 19-6008 | Radcure |
| E | Tripropylene Glycol Diacrylate | Sartomer SR-306 | ARCO |
| F | Polyethylene Glycol Diacrylate | Sartomer SR-344 | ARCO |
| G | Propoxylated Neopentyl Glycol Diacrylate | Photomer 4127 | Diamond Shamrock |
| H | N—Vinyl-2-Pyrrolidone | V-Pyrol | GAF |

The amounts are given in weight percent.

EXAMPLES 1-22

A series of six formulations of EB/UV curable resins were prepared. Compositions of these formulas are set forth in Table 3, and test data are summarized in Table 3a.

About 4 pph of Irgacure 184 photoinitiator was added to 75-100 gram amounts of each of the six resins. Each resin was coated in 1-2 mil, (0.001-0.002 in) and 3-4 mil (0.003-0.004 in) thick coatings onto embossed, 1 mil (0.001 in) thick diaper polyethylene, and the coatings were passed under UV light to polymerize the resins.

Formulations 1 and 3 did not fully cure, regardless of the amount of UV exposure or coating thickness. Formulation 5 felt cured after 3 double passes of UV light for only the 3-4 mil coating, but would not cure when applied in thinner coating layers. Formulations 2, 4 and 6 felt cured after 3 or 4 passes under the UV light, but the surfaces felt almost tacky and adhered when contacted together.

Formulas 2, 4, 5 and 6 were coated in 1-2 mil and 3-4 mil thicknesses onto the male side of the embossed, 1 mil diaper polyethylene and exposed to 3, 4, 5 and 6 double passes of UV light. A tape refastenability test was performed on the uncoated side of the polyethylene. This test was performed with a control roll of 3M diaper tape, and the same roll of tape was employed to test 1 mil and 1.5 mil thick diaper polyethylene. The roll of diaper tape had an average peel adhesion value of about 500 gm.

Twenty of the UV cured resin coated polyethylene samples were subjected to the standard refastenability test and exhibited substantially no tear or stretch. The average mean peel value was 512 grams with a standard deviation of 36 grams.

The average mean peel value for seven uncoated 1.5 mil Clopay polyethylene samples was 516 grams with a standard deviation of 26 grams.

On ten, 1-mil, thick, non-reinforced diaper poly samples tested, seven exhibited severe stretch.

TABLE 3

| | Resin Code | | | |
|---|---|---|---|---|
| | A | D | E | F |
| Formula # | Wt. percent of resin in formulation | | | |
| 1 | 36 | 9 | 55 | — |
| 2 | 36 | 9 | — | 55 |
| 3 | 45 | 9 | 46 | — |
| 4 | 45 | 9 | — | 46 |
| 5 | 55 | 9 | 36 | — |
| 6 | 54 | 9 | — | 37 |

TABLE 3a

| Sample # | Formula # | Viscosity (cP) | Refast. (Grams Peel Force) | Surface (by feel) |
|---|---|---|---|---|
| 1 | 1 | 325 | N/A | wet |
| 2 | 2 | 725 | 503 | tacky |
| 3 | 2 | 725 | 512 | tacky |
| 4 | 2 | 725 | 508 | tacky |
| 5 | 2 | 725 | 515 | tacky |
| 6 | 2 | 725 | 487 | tacky |
| 7 | 3 | 700 | N/A | wet |
| 8 | 4 | 1050 | 508 | tacky |
| 9 | 4 | 1050 | 458 | tacky |
| 10 | 4 | 1050 | 546 | tacky |
| 11 | 4 | 1050 | 516 | tacky |
| 12 | 5 | 1600 | 560 | tacky |
| 13 | 5 | 1600 | 542 | tacky |
| 14 | 5 | 1600 | 505 | tacky |
| 15 | 5 | 1600 | 466 | tacky |
| 16 | 5 | 1600 | 548 | tacky |
| 17 | 6 | 2150 | 507 | tacky |
| 18 | 6 | 2150 | 480 | tacky |
| 19 | 6 | 2150 | 501 | tacky |
| 20 | 6 | 2150 | 522 | tacky |
| 21 | 6 | 2150 | 500 | tacky |

TABLE 3a-continued

| Sample # | Formula # | Viscosity (cP) | Refast. (Grams Peel Force) | Surface (by feel) |
|---|---|---|---|---|
| 22 | 6 | 2150 | 566 | tacky |

EXAMPLES 23-34

The resin formulations listed in Table 4 where prepared. The resins were coated onto embossed, 1 mil polyethylene film with an average coating thickness of 2 mils, and the resin coatings were cured with UV light until the surface felt dry. The resin coatings were tested for adhesion to the film by use of the crosscut adhesion test, and the degree of brittleness of the coatings was evaluated by the crease method. The film reinforcement functionality of the coatings was evaluated by use of the tape refastenability test, using a tape with an average peel force value against diaper poly between 690-800 gm. Tensile modulus and percent elongation values for the cured resins were also recorded. The results of the tests are shown in Table 5.

TABLE 4

| Formula | Composition (wt. %) | | | |
|---|---|---|---|---|
| | A | D | F | H |
| 6 | 55 | 9 | 36 | |
| 7 | 60 | | 30 | 10 |
| 8 | 60 | | 20 | 20 |
| 9 | 65 | | 10 | 25 |

TABLE 5

| Sample # | Formula # | Crease (mil) | Crosscut (#/25) | Refastenability (avg mean peel) | Tensile secant modulus (psi) | % elong |
|---|---|---|---|---|---|---|
| 23 | 6 | 1-2 | 7 | film deformation | N/A | N/A |
| 24 | 6 | | 10 | film deformation | N/A | N/A |
| 25 | 6 | | 14 | film deformation | N/A | N/A |
| 26 | 7 | 2-3 | 9 | 690 | 895 | 51 |
| 27 | 7 | | 9 | 717 | 885 | 51 |
| 28 | 7 | | 19 | 793 | 810 | 43 |
| 29 | 8 | 8-10 | 21 | 757 | 1195 | 71 |
| 30 | 8 | | 22 | 749 | 1335 | 43 |
| 31 | 8 | | 22 | 759 | 1500 | 55 |
| 32 | 9 | N/A | 23 | N/A | 1830 | 59 |
| 33 | 9 | N/A | 25 | N/A | 1425 | 63 |
| 34 | 9 | N/A | 21 | N/A | 1590 | 103 |

The test results on Table 5 show that N-vinyl-2-pyrrolidone (NVP) is superior to polyether triacrylate as a reactive diluent for UV curable formulations designed for 1 mil PE film reinforcement. The test results also show that by increasing the NVP content in the formulation from 10 to 20%, the ductility, adhesion, tensile modulus, and elongation can be increased. Formula #4 shows that the tensile properties can be further improved by altering the formulation composition.

EXAMPLES 35-37

In order to further optimize the formulation and to study the curing speed of the UV curable resin coatings, the formulas 10, 11, and 12 were UV cured by passing 1-2 mil coatings on 1 mil PE film under four 300-W/in Fusion Systems UV lamps set at the optimum distance of 2.1 inches from the web. All 3 formulations contained 25% of ingredients G and H each. The oligomers for each are listed in Table 6. All of the coatings had sufficient cure for testing.

The coatings were measured for density by stripping off small portions and immersing them in salt solutions of varying density, and observing whether they would sink or float. Samples measuring 6×4 inches were cut and weighed. The coating density and average wt. of the 1 mil PE film substrate were used to calculate the average coating thickness by weight.

The samples were then measured for stiffness using an Electronic Digital Read-out Handle-O-Meter, Model 211-5, from Thwing Albert Instrument Company, Philadelphia, PA, equipped with flat (not curved) plates. A ¼ inch gap setting on the Handle-O-Meter was used. The samples were placed in the sample chamber with the 6 inches along the lengthwise direction of the machine.

After stiffness readings were taken for each sample, the Tape Refastenability Test using a 2″ poly gauge length and a test speed of 300 mm/min was performed on each sample.

Figure 7:
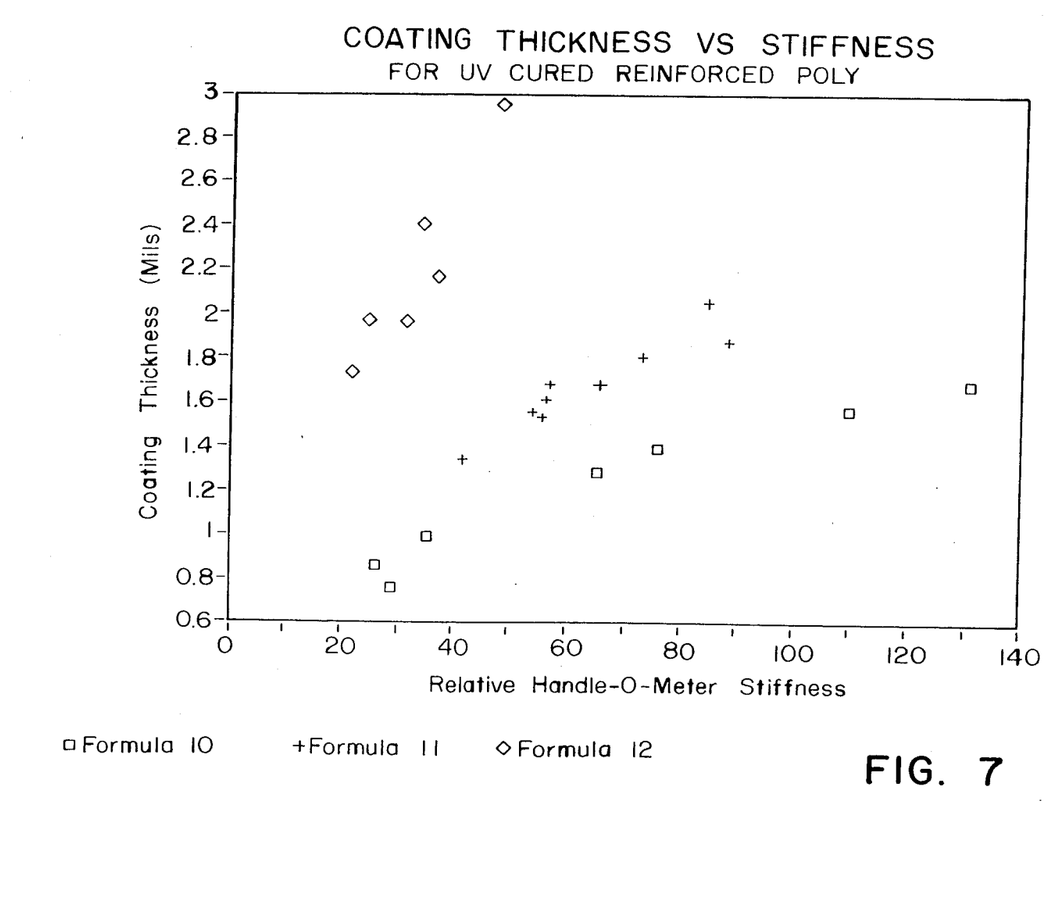
FIG. 7 is a chart which representatively shows the effect of coating thickness versus stiffness.

FIG. 7 representatively shows the relationship between coating thickness and Handle-O-Meter stiffness reading. Table 6a shows the stiffness at 1.6 mils coating thickness (determined from weight calculations), the formula's Modulus of Elasticity and Elongation at break, and ratio of samples (failed/passed) for the refastenability test.

TABLE 6

| Formula | Oligomer Type and Percent (wt. %) | | | | |
|---|---|---|---|---|---|
| | A | B | C | G | H |
| 10 | 0 | 50 | 0 | 26 | 25 |
| 11 | 30 | 25 | 0 | 25 | 25 |
| 12 | 0 | 0 | 50 | 25 | 25 |

TABLE 6a

| Formula | Stiffness Reading at 1.6 mil | Modulus (psi) | Percent Elongation | Refast. Ratio |
|---|---|---|---|---|
| 10 | 120 | 20,000 | 23 | 1/2 |
| 11 | 60 | 12,000 | 24 | 1/2 |
| 12 | 20 | 2,500 | 60 | 0/3 |

Having thus described the invention in rather full detail, it will be readily apparent that various changes and modifications can be made without departing from the spirit of the invention. Such changes and modifications are all contemplated as being within the scope of the invention as defined by the subjoined claims.

We claim:

1. A method for reinforcing a substrate to provide an attachment zone for a pressure-sensitive adhesive tape, comprising the steps of:
   a. coating at least a portion of the surface of said substrate with a layer of material which is capable of being polymerized by a high-energy-radiation; and
   b. polymerizing said coating material with a source of said high-energy-radiation to form a reinforcement layer affixed to said substrate, thereby providing an attachment zone against which said tape can be refastenably adhered, wherein said attachment zone has a peel tear strength greater than a peel adhesion value of said pressure-sensitive adhesive tape.

2. A method as recited in claim 1, wherein said coating material includes at least one compound selected from the group consisting or urethane acrylate acrylic oligomers, acrylated acrylic oligomers and epoxyacrylate acrylic oligomers.

3. A method as recited in claim 1, wherein said coating material is composed of a high-energy-radiation curable admixture consisting essentially of:
   a. about 30–60 wt. % of at least one compound selected from the group consisting of urethane acrylate acrylic oligomers, acrylated acrylic oligomers and epoxyacrylate acrylic oligomers;
   b. about 30–50 wt. % of at least one compound selected from the group consisting of monofunctional acrylate monomers, difunctional acrylate monomers and acrylic monomers; and
   c. about 0–15 wt. % of trifunctional acrylate monomers, with the proviso that the component materials total 100 wt. %.

4. A method as recited in claim 1, wherein said coating material is composed of a admixture consisting essentially of:
   a. about 30–70 wt. % of at least one compound selected from the group consisting of urethane acrylate acrylic oligomers, acrylated acrylic oligomers and epoxyacrylate acrylic oligomers;
   b. about 10–40 wt. % of N-vinyl-2-pyrrolidone; and
   c. about 5–40 wt. % of at least one of the compounds selected from the group consisting of polyethylene glycol diacrylate and propoxylated neopentyl glycol diacrylate, with the proviso that the component materials total 100 wt. %.

5. A method as recited in claim 4, wherein said coating material consists essentially of
   a. about 60 wt. % of a urethane acrylate oligomer;
   b. about 20 wt. % of N-vinyl-2-pyrrolidone; and
   c. about 20 wt. % of polyethylene glycol diacrylate.

6. A method as recited in claim 4, wherein said coating material consists essentially of:
   a. about 50 wt. % of a urethane acrylate oligomer;
   b. about 25 wt. % of N-vinyl-2-pyrrolidone; and
   c. about 25 wt. % of propoxylated neopentyl glycol diacrylate.

7. A method as recited in claim 1, wherein:
   a. said coating material further includes an operable amount of a photoinitiator; and
   b. said source of high-energy-radiation is a source of UV radiation.

8. A method as recited in claim 1, wherein said source of high-energy-radiation is an electron beam energy source.

9. A method as recited in claim 1, wherein said curing step (b) produces a cohesive bond between said substrate and said coating material.

10. A method as recited in claim 9, wherein said cohesive bond has a tape peel strength of at least about 700 gm/in.

11. A method as recited in claim 9, wherein said cohesive bond provides a cross-cut adhesion test value of at least about 22.

12. A method as recited in claim 9, wherein said curing step (b) forms a reinforcement layer that has a crease test value of at least about 0.00508–0.02032 cm.

13. A method as recited in claim 1, wherein said coating material forms a layer about 0.025–0.075 mm thick on said substrate.

14. A reinforced composite article, comprising:
   a. a substrate which by itself has a peel tear strength less than a peel adhesion value of an adhesive tape appointed for attachment to said substrate; and
   b. a reinforcement coating layer affixed on at least a portion of a surface of said substrate, said coating composed of a polymerized acrylic oligomer and providing a reinforced substrate which has a peel tear strength greater than the peel adhesion value of the adhesive tape appointed for attachment thereto, and said acrylic oligomer composed of at least one compound selected from the group consisting urethane acrylate acrylic oligomers, acrylated acrylic oligomers and epoxyacrylate acrylic oligomers.

15. A composite article as recited in claim 14, wherein said reinforcement coating material has been formed by radiation curing a high-energy-radiation curable composition consisting essentially of:
   a. about 30–60 wt. % of at least one compound selected from the group consisting of urethane acrylate acrylic oligomers, acrylated acrylic oligomers and epoxyacrylate acrylic oligomers;
   b. about 30–50 wt. % of at least one compound selected from the group consisting of monofunctional acrylate monomers, difunctional acrylate monomers and acrylic monomers; and
   c. about 0–15 wt. % of trifunctional acrylate monomers, with the proviso that the component materials total 100 wt. %.

16. A composite article as recited in claim 14, wherein said composite has a Handle-O-Meter stiffness reading of less than about 120.

17. A composite article as recited in claim 14, wherein said substrate is comprised of a plastic film.

18. A composite article as recited in claim 14, wherein said substrate is comprised of a thermoplastic polyolefin film selected from the group consisting of polyethylene film and polypropylene film.

19. A composite article as recited in claim 14, wherein said reinforced article is constructed for use as an attachment zone against which a pressure-sensitive adhesive tape is releasably adhered in a tape closure system.

20. A composite article as recited in claim 19, wherein said tape closure system is constructed to fasten a disposable garment onto a wearer.

21. A composite article as recited in claim 19, wherein said tape closure system is constructed to fasten a disposable diaper onto a infant.

22. A tape closure system, comprising:
   a. a tape member which includes thereon a layer of pressure-sensitive adhesive having a peel adhesion value;
   b. an attachment substrate composed of a polyolefin film material for receiving an adhesive contact with said tape member; and
   c. a reinforcement layer which is affixed to said attachment substrate and at least in part composed of a polymerized, urethane acrylate acrylic oligomer which has been cured by exposure to a high-energy-radiation;
   d. wherein the combination of said attachment substrate and said reinforcement layer provides a peel tear strength at the attachment substrate which is greater than the peel adhesion value of said pressure-sensitive adhesive.

23. A tape closure system, comprising:

a tape member which includes thereon a layer of pressure-sensitive adhesive having a peel adhesion value;

an attachment substrate for receiving an adhesive contact with said tape member; and a reinforcement layer affixed to said attachment substrate, said reinforcement layer at least in part composed of a material which is selected from the group consisting of urethane acrylate acrylic oligomers, acrylated acrylic oligomers and epoxyacrylate acrylic oligomers, and which has been polymerized by exposure to a high-energy-radiation;

wherein the combination of said attachment substrate and said reinforcement layer provides a peel tear strength at the attachment substrate which is greater than the peel adhesion value of said pressure-sensitive adhesive.

24. A tape closure system as recited in claim 23, wherein said reinforcement layer is provided by a high-energy-radiation curing of an applied coating material composed of high-energy-radiation curable admixture consisting essentially of:

a. about 30-60 wt. % of at least one compound selected from the group consisting of urethane acrylate acrylic oligomers, acrylated acrylic oligomers and epoxyacrylate acrylic oligomers.

b. about 30-50 wt. % of at least one compound selected from the group consisting of monofunctional acrylte monomers, difunctional acrylate monomers and acrylic monomers; and c. about 0-15 wt. % of trifunctional acrylate monomers, with the proviso that the component compounds total 100 wt. %.

25. A tape closure system as recited in claim 24, wherein said coating material consists essentially of:

a. about 40-60 wt. % of at least one compound selected from the group consisting of urethane acrylate acrylic oligomers, acrylated acrylic oligomers and epoxyacrylate acrylic oligomers;

b. about 10-25 wt. % of N-vinyl-2-pyrrolidone; and c. about 5-25 wt. % of at least one of the compounds selected from the group consisting of polyethylene glycol diacrylate and propoxylated neopentyl glycol diacrylate.

26. A disposable garment, comprising:

a fluid permeable facing sheet;

a backing sheet which includes a fluid impermeable layer and is attached to selected areas of said facing sheet;

an absorbent pad disposed between said facing sheet and said backing sheet; and one or more pressure-sensitive tape strips which has attached portions affixed to selected portions of said garment and which have unattached portions configured to adhesively engage predetermined attachment zones located on other selected portions of said garment; wherein said backing sheet has a peel tear strength less than a peel adhesion value of said tape strips;

said attachment zones include a renforcement layer, which is composed of a polymerized urethane acrylate acrylic oligomer and is affixed to said backing sheet; and said reinforced attachment zones have a peel tear strength which is greater than the peel adhesion value of said tape strips.

* * * * *